(12) United States Patent
Schumacher

(10) Patent No.: US 9,861,724 B2
(45) Date of Patent: Jan. 9, 2018

(54) METHOD FOR FUSION OF FRACTURED OR VOIDED STERNUM POST STERNOTOMY

(71) Applicant: Mark Schumacher, Maitland, FL (US)

(72) Inventor: Mark Schumacher, Maitland, FL (US)

(73) Assignee: FUSION INNOVATIONS, LLC, Sanford, FL (US)

( * ) Notice: Subject to any disclaimer, the term of this patent is extended or adjusted under 35 U.S.C. 154(b) by 355 days.

(21) Appl. No.: 14/453,542

(22) Filed: Aug. 6, 2014

(65) Prior Publication Data
US 2015/0045906 A1  Feb. 12, 2015

Related U.S. Application Data

(60) Provisional application No. 61/862,952, filed on Aug. 6, 2013.

(51) Int. Cl.
| | | |
|---|---|---|
| *A61B 17/80* | (2006.01) |
| *A61L 27/36* | (2006.01) |
| *A61L 27/10* | (2006.01) |
| *A61L 27/12* | (2006.01) |
| *A61L 27/24* | (2006.01) |
| *A61L 27/50* | (2006.01) |
| *A61B 17/68* | (2006.01) |
| *A61B 17/82* | (2006.01) |

(52) U.S. Cl.
CPC .......... *A61L 27/3608* (2013.01); *A61B 17/68* (2013.01); *A61L 27/10* (2013.01); *A61L 27/12* (2013.01); *A61L 27/24* (2013.01); *A61L 27/50* (2013.01); *A61B 17/8076* (2013.01); *A61B 17/823* (2013.01); *A61L 2430/02* (2013.01)

(58) Field of Classification Search
CPC .......................... A61B 17/8076; A61B 17/823
See application file for complete search history.

(56) References Cited

U.S. PATENT DOCUMENTS

| | | | |
|---|---|---|---|
| 9,101,475 B2 * | 8/2015 | Wei ........................... A61F 2/30 |
| 2004/0010256 A1 * | 1/2004 | Gabbay ................ A61B 17/823 |
| | | | 606/71 |
| 2011/0082497 A1 * | 4/2011 | Deslauriers ...... A61B 17/00491 |
| | | | 606/213 |

* cited by examiner

*Primary Examiner* — David Bates
(74) *Attorney, Agent, or Firm* — Timothy H. Van Dyke; Beusse, Wolter, Sanks & Maire PLLC

(57) ABSTRACT

Disclosed herein are improved surgical techniques for repairing bone defects in a sternum during a sternotomy procedure and implants adapted for such techniques. In an exemplary embodiment, provided is a fusion strip made of an osteoconductive material and of a dimension that is especially adapted for improved repair of sternal bone defects.

14 Claims, 12 Drawing Sheets

METHOD FOR FUSION OF FRACTURED OR VOIDED STERNUM POST STERNOTOMY

BACKGROUND

The use of various forms of demineralized bone matrix (DBM) has been a standard practice in Orthopedic surgery for at least 30 years. DBM is an osteoconductive and osteoinductive material that resorbs and is replaced with host bone (patient's bone) during the healing process. Its main component, demineralized cortical bone matrix, is derived from donor human tissue (allograft bone) that has been aseptically processed and contains various growth factors including osteoinductive proteins. Most DBM is finely granulated cortical bone, which is mixed with a biocompatible carrier that allows the product to exist in the form of a putty, paste, or gel.

BRIEF DESCRIPTION OF THE DRAWINGS

FIG. 9 depicts a side view 9a of an example of a fusion strip embodiment and a perspective view 9b of the fusion strip embodiment shown in FIG. 9a.

FIG. 15 shows another embodiment of a fusion strip that has varied width and thickness dimensions.

DETAILED DESCRIPTION

Figure 1:
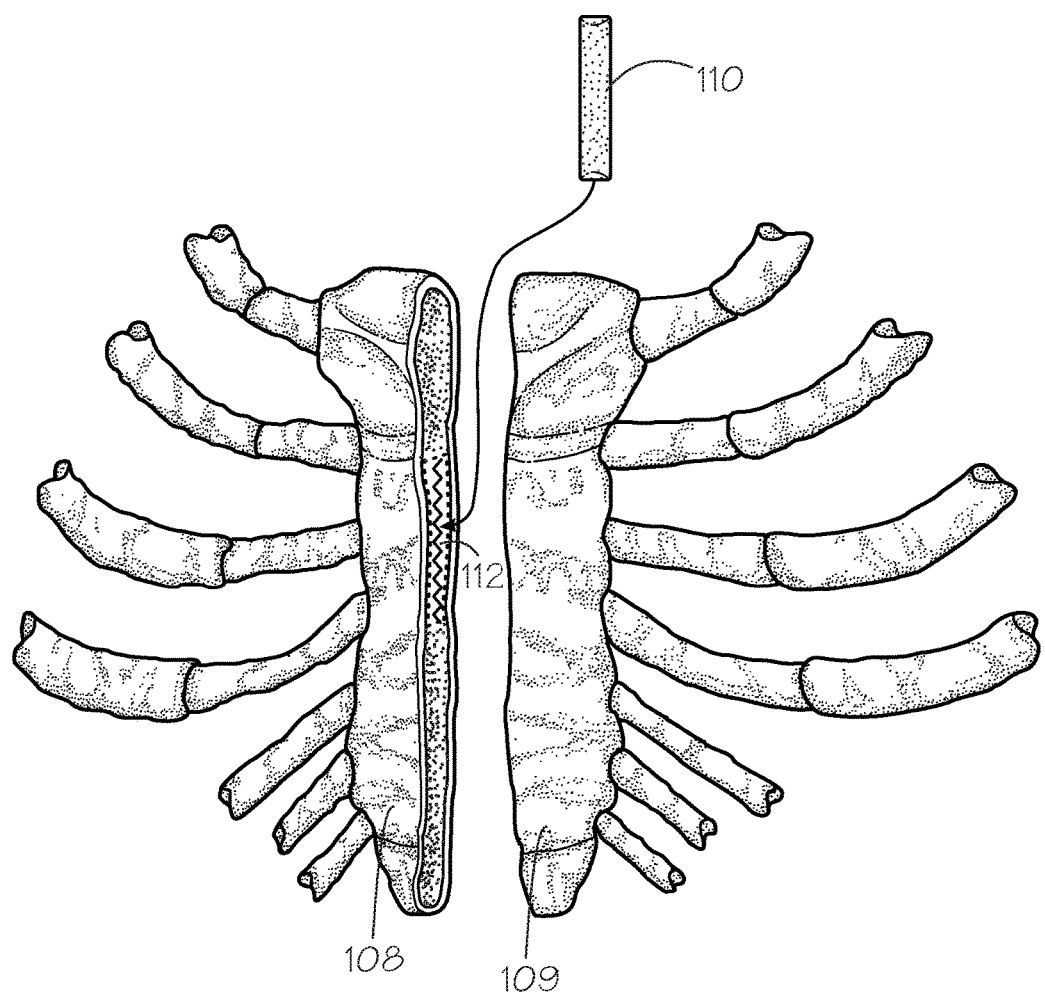
FIG. 1 depicts the use of a fusion strip embodiment in a sternotomy procedure in a sternum having a defect.

Unless defined otherwise, all technical and scientific terms used herein have the same meaning as is commonly understood by one of ordinary skill in the art to which this disclosure belongs. All patents, applications, published applications and other publications are incorporated by reference in their entirety. In the event that there are a plurality of definitions for a term herein, those in this section prevail unless stated otherwise.

While DBM has been known, its use has been limited to specific fields of medicine. It has been realized that the use of DBM by cardiac surgeons or plastic surgeons has not been developed. A main reason that DBM historically could not be used in the sternum is because most common forms of DBM tend to migrate after placement in the bone.

Cadaveric tissue is a precious and unique material. The form and use of cadaveric-derived allograft material is directly connected to available harvesting and processing techniques as well as the natural architecture of the tissue itself. Accordingly, there are limits on the types of products that can be produced from cadaveric tissue. Indeed, there are multiple patents surrounding the production of new types of implants that are only made possible by new processing techniques.

Recent technical advancements have resulted in bone banks being able to create a new variation of DBM by harvesting specifically-sized strips of cancellous bone and process them for use in surgery. Another new variation is to machine cortical bone into shavings that are then compressed into various shaped molds and demineralized. The resultant product can be uniquely shaped and utilized in spine, orthopedic surgery, foot and ankle surgery, and Cranio-maxillofacial surgery, to name a few. These demineralized allograft bone products have no added carrier and thus exist as 100% DBM.

One aspect of the disclosure is the utilization of DBM or bone graft substitute strips of a unique size and configuration (hereinafter referred to as fusion strips) that are adapted for safe use in the sternum of patients by cardiothoracic surgeons as a method to repair defects or voids in the sternotomy site. There are limited sources of these strips; only a few bone banks in the US currently make the demineralized cancellous allograft strips. It is believed that none of these tissue banks, or any orthopedic or cardiac company has developed the use of demineralized cancellous strips or any other form of DBM in the sternum for sternotomy procedures. According to a specific embodiment, disclosed herein is the use of demineralized allograft bone (e.g. cancellous or cortical) in a form of a strip for implementation in the surgical wound to the sternum following open heart surgery.

The size of the size of the fusion strip that is particularly adapted for use in the sternum may be 3-12×45-60×3-8 mm (width×length×thickness). In a more specific embodiment, the dimension of the fusion strip is approximately 5×50×5 mm or approximately 7×50×5 mm. This size is currently made by only 2 bone banks in the US [Bone Bank Allografts and Bacterin]. The term "approximately" as it applies to dimensions means that each recited dimension may deviate up to 2 mm or 10 percent, whichever is greater. Thus, for example, approximately 100 mm means 100 mm or from 90 mm to 110 mm; or approximately 10 mm means 10 mm or from 8 mm to 12 mm. Also contemplated is the use of fusion strips having a slightly larger width, e.g., 9-12×45-60×3-8 mm, or in a more specific embodiment, the configuration is approximately 10×50×5 mm or approximately 12×50×5.

According to an alternative embodiment, the fusion strips are processed (e.g. cut) to produce a male and female notch in the lateral sides or ends of the graft, thus creating a simple joint, similar to a puzzle piece or wooden toy train tracks. This will then allow two or more pieces to be joined together with or without a biologically compatible glue or suture, prior to implantation.

Technique:

Cardiac surgeons most commonly use a sternotomy technique (splitting the breastbone with a powered saw) to gain access to the heart. The breastbone is ideally sawed longitudinally down the midline of the sternum (median sternotomy). At the end of the surgery, both halves of the sternum (hemi sternum) are approximated (brought back together) and secured with monofilament stainless steel cerclage wire. There are modified versions of the sternotomy technique that include a combination of longitudinal and transverse incisions into the sternum as well. Some surgeons use cables, or plates and screws to secure the sternum as an alternative method. Most patients have adequately hard and robust sternal bone quality, which tends to heal well following surgery. However, there are increasing numbers of older and sicker patients in recent years, who have poor sternal bone quality. Up to 15% of heart patients have this problem. The fusion strip is most commonly used in heart patients who have osteoporosis, or other conditions that cause their bone to degenerate, thus creating very soft or voided areas of their cancellous (spongy) sternal bone. It also may be used in the sternums of heart patients that have any type of fracture, gap or void at the sternotomy site, not necessarily associated with osteoporosis.

The shorter, upper part of the human sternum is referred to as the manubrium, while the longer, central part is referred to as the sternal body. The bottom part of the sternum is called the xyphoid process. When a patient is a candidate for this fusion strip, typically 2 small pieces (7×50×5 mm) are placed longitudinally along the sternal body, in between the sternotomy site.

The sternal body is usually more negatively affected by osteoporosis than the manubrium. It is at the surgeon's discretion whether the manubrium needs be grafted with a fusion strip. If necessary, the larger (12×50×5 mm) fusion strip is placed in the manubrium in addition to the 2 smaller pieces in the sternal body. So, 2 or 3 pieces are routinely used on a typical case. In an alternative embodiment, a different sizing option for treatment of the sternal body is provided: 7×45×5 mm. In this case, three pieces might be used from the xyphoid all the way to the top of the sternal body. And, this would total 4 pieces if the larger piece is also used in the manubrium. This is all dependent on the dimensions of the patient's sternum and severity of the voids.

Before implantation, each piece of bone graft is typically rehydrated for several minutes in saline, blood, or bone marrow aspirate or some other suitable liquid, following the instructions from the bone bank.

Also, according to another embodiment, the fusion strip may include varied dimensions along the length of the strip. For example, the fusion strip may have the side profile that shows a section of the strip having one width and another section that has a larger or smaller width. In a specific example, the side profile of the fusion strip resembles a paddle. In an even more specific embodiment, the fusion strip comprises a first section that is approximately 100 mm in length and approximately 7 mm wide and section contiguous to the first section that is approximately 50 mm long and approximately 12 mm wide.

Example 1

Before implantation, in this example, the fusion strip needs to be rehydrated, which is typically done by using saline, blood or some other suitable fluid for a minimum of 5 minutes. Then once it is rehydrated and spongy, the graft is taken out of the saline and gently squeezed against a surgical towel, so as to remove most of the saline. The graft will still remain spongy and pliable at this point. This is done immediately prior to implantation in the sternotomy site. Then, once it is placed into the site, following the technique described below, it will absorb the bone marrow, accomplishing two tasks. It will wick up (absorb) live osteogenic cells from the marrow, which is critical to allow the bone healing cascade to initiate within the graft. Secondly, it acts as a hemostatic agent because the trabelcular structure of the cancellous bone graft fusion strip offers a perfect scaffold for blood clots to form within.

If further hemostatic action is desired, the rehydrated fusion strip can be soaked in a thrombin or fibrinogen solution, or anhydrous thrombin powder or platelet gels can be applied to it before implantation. Other possible hemostatic agents that can be applied to this bone graft include various oxidized cellulose products, microcrystalline collagens, gelatins, or microporous polysaccharide hemospheres. Bone wax should always be avoided for hemostasis in combination with the bone graft. It also should not be applied to the edges of the sternal halves at the beginning of the surgery. It may act as a permanent barrier and inhibitor of bone growth. The performance of the bone graft will be constrained.

When the 1 to 4 fusion strips of are implanted, it is important that they form one long, continuous piece as it is placed. A big challenge with implanting the fusion strips onto the edge of a sternal half at the sternotomy site, is how to keep it in place until the sternum is approximated. One must prevent the fusion strip from falling down from the edge of the sternal half onto the heart or somewhere else in the mediastinum. The first described method is for the surgeon to place the first fusion strip with forceps along the affected edge of either the left or right sternal half, and then to place 2 to 3 mattress style sutures around or through the center of the fusion strip and through the cortices of the host bone so as to gently hold the graft in place. Then the second, third, and/or fourth fusion strip is contiguously placed and sutured in a similar fashion. It is important not to suture the fusion strip too tightly, or else it will compress the strip, thus compromising its ability to fill in the bone voids of the other sternal half, once approximation of the sternum has taken place. The cerclage wire or sternal cables can be placed in the sternum either before or after placement of the fusion strip, depending on the surgeon's preference.

A variation of this method uses biologically compatible glues or fibrin type sealants, or other hemostatic products, as described above, to adhere each piece of the fusion strip in position along one side of the sternal half in a similar fashion as the aforementioned mattress suture method or they can also be used to connect (glue) 2 or more fusion strips before they are placed into the sternum. The puzzle piece-fashioned joints will be machined by the bone bank onto each fusion strip. This will create more surface area between the pieces, allowing better bonding of the glue. If suture is used to connect the pieces, this joint will serve as a junction point that will accept placement of the suture.

It should be borne in mind that the reference to sternal half or halves is used in a broader sense to pertain to any section of the sternum that is typically formed during a sternotomy and not to just a section representing a one-half of a sternum. Also, the sternum may, but not necessarily be cut into more than two sections, or halves.

Example 2

A second implantation method is to place each piece of the fusion strip, one at a time, into the sternotomy site while simultaneously tensioning the wires. First, place all of the cerclage wire or cable in the sternum using the surgeon's routine technique. Then the wires or cables are tensioned and the sternum is brought to within roughly 5 mm of being fully approximated. At this point, the surgeon or assistant will use forceps to place the first piece of the fusion strip longitudinally in between the two sternal halves, making sure that the fusion strip is placed into the realm of the voided cancellous bone. The first piece is usually implanted in the most superior portion of the affected sternal bone. Then, while holding the first piece in place with forceps, that portion of the sternum is further approximated and the wires can be crossed and twisted once or twice to maintain approximation, thus holding the fusion strip in place. Then working inferiorly (down the sternum) the second and successive pieces are placed contiguously to the first piece with forceps using the aforementioned technique. Finally, all the wires are twisted, or the cables are tensioned in the routine manner to fully approximate and secure the sternum.

Example 3

In a variation of the method, each piece of the fusion strip (between 2 and 4) after rehydration, may be wrapped in a thin layer of resorbable gauze-like material, which would roll them together in a cigar-like fashion. This could then be placed against one side of the sternal half in the sternotomy site, as one unit, rather than three or four separate pieces. For example, a commonly available hemostatic product, Surgicel® original, from Ethicon Biosurgery could be used in this case. A 2×6 inch strip, for example, of Surgicel® would be laid on a sterile towel. Each rehydrated fusion strip would be placed linearly onto the Surgicel® strip. Then the fusion strips would be rolled one time to encapsulate the them, like rolling a cigar. Excess Surgicel® material would be trimmed off at this point. It can also be rolled onto three sides of the fusion strips, leaving the portion of graft that bridges to the other sternal half uncovered. Then, the entire piece would be gently tucked into the voided area of the sternotomy site. The sternum would then be closed in a routine manner, as described above.

Example 4

Another variation of the above method would use an absorbable surgical tape or mesh to gently fasten each piece of the fusion strip in place along the sternotomy site. A small, narrow piece of the surgical tape would go from the near cortex of the sternum down and around the fusion strip and then to the underside of the far sternal cortex (similar to placement of sutures).

Example 5

A third method of implantation describes how to implant the fusion strip when the surgeon is also using plates and screws. Most plates are implanted onto the sternum after the sternum is approximated with cerclage wire, as described above. In those instances, either of the aforementioned methods for implanting the fusion strip can be used prior to plate and screw implantation.

A newer generation of plates, specifically the Tritium™ Sternal Cable Plate from Pioneer Surgical, includes a cable that goes through the plate and around the sternum. This cable is first placed around the sternum, in a similar fashion as a cerclage wire is implanted. Then the cable is tensioned and crimped to help approximate the sternum. Finally, the screws are placed into the plate. If the surgeon chooses to use the fusion strip in conjunction with a Tritium™ Sternal Cable Plate or any other similar plate, the fusion strip may first be loosely sutured or glued to the underside of the plate. (see FIGS. 12 and 13) Then the plate is placed onto the desired portion of the sternum and the cable is then tensioned following the standard technique.

Other Considerations

In each aforementioned method of implanting the fusion strip, the orientation of the strip against the edge of the sternotomy site is generally as follows: the width dimension is typically laid against the side of the bone where the void or gap is located. For purposes of explanation only, and not intended to limit the scope of the invention in any way, when using a specific example, such as a 7×50×5 mm (width× length×thickness) fusion strip, the 7 mm dimension is laid against the side of the bone and covers from the near to the far cortex (superficial to deep), while the 5 mm dimension bridges in between the left and right sternal halves, and the 50 mm portion runs up and down the length of the sternum, in a superior/inferior direction. If necessary, the fusion strip can be rotated 90 degrees, allowing the 7 mm dimension to bridge between both sides. If the size of the sternal body is quite large, then two to three of the 12×50×5 mm fusion strips should be used instead of the smaller size. If the voids are large, the 12 mm portion can be rotated transversely to bridge between the left and right sternal halves. If the voids are significant, separate fusion strips are placed along both sides of the sternal halves at the sternotomy site. If any combination of transverse and median sternotomy techniques are used, either size fusion strip may be used to fill voids, at the surgeon's discretion.

Another important use of the fusion strip is for treatment of sternal non-unions. In these cases, the surgeon must reopen the sternum and pull out the old wires or cables. He must then debride the fibrous tissue within the fracture gap of the non-united bone. This debridement must be done until the bleeding margins on the ends of the sternal bone are exposed. Very often a rasp must be also used to remove fibrous and devitalized tissues. At this point the sternum is rewired and approximated. In many instances, the edges of the sternal halves do not meet together well (have gaps), because of the debridement process. Therefore placing the fusion strip between the edges is warranted. The fusion strip will compress if there is no gap, and will expand like a sponge into any gaps along the edges of the sternal bone. The implantation technique in this case may be similar to that as mentioned above. In this case, perhaps only one fusion strip may be necessary.

Synthetic calcium osteoconductive bone graft substitutes could be machined into identical or longer lengths as the human allograft bone described above. These bone substitute material composite grafts are typically made from calcium sulphate or calcium phosphate materials. Synthetic bone substitutes are also made from the following: ceramic hydroxyapatites, bioglasses, coralline hydroxyapatites, tricalcium phosphate, or bovine collagen, to name a few. They emulate human demineralized cancellous bone, having a similar size interconnected porosity, which is the scaffold for cellular ingrowth.

Alternatively, a cortical bone based DBM material formed from cortical bone pieces, such as shavings, that are compressed into various molds may be used instead of demineralized cancellous bone. Alternatively, the cortical bone based DBM material includes a physiologically acceptable carrier such as, but not limited to, collagen, gelatin and/or lecithin and the like. The cortical bone based DBM may comprise 30-100 percent demineralized cortical bone. In a more specific example, the cortical bone based DBM may comprise 90-100 percent demineralized cortical bone. A non-limiting representative example of a synthetic fusion strip for the sternal body might be, for example, approximately 7×135×5 mm, which is longer than what can be typically achieved from demineralized cancellous bone. Various other heights and lengths could be made to treat patients with larger or smaller sternal dimensions.

Illustrated Examples

Figure 2:
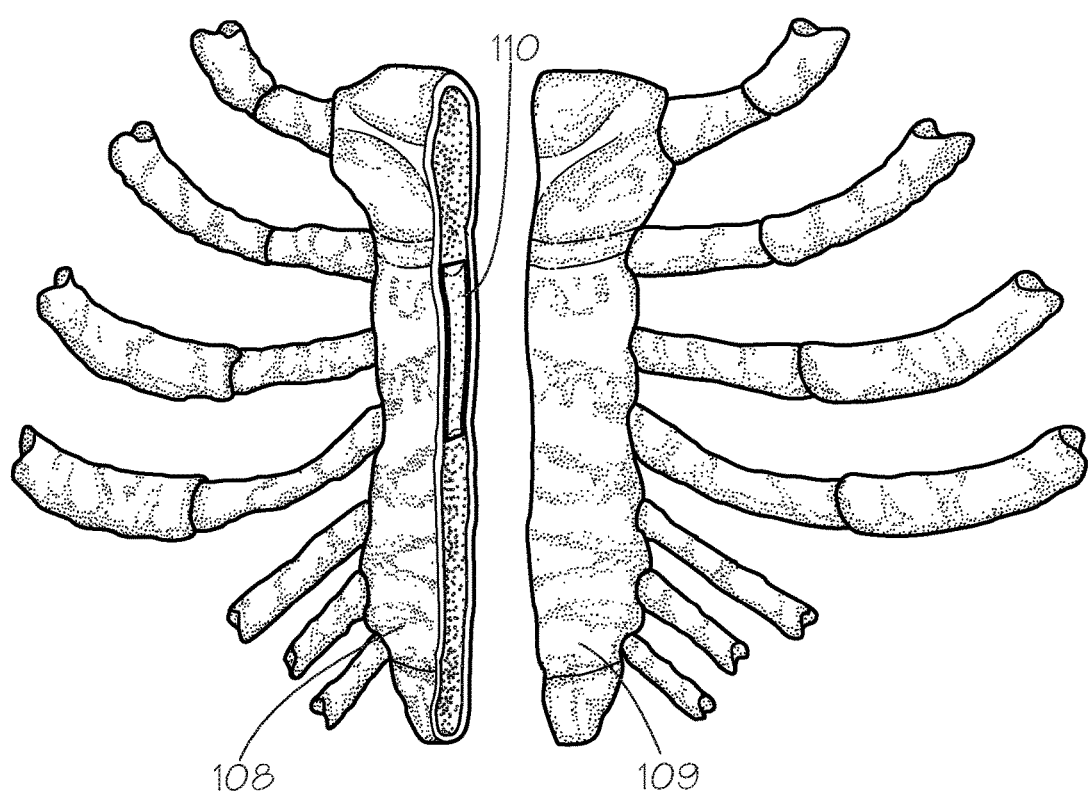
FIG. 2 shows the positioning of a fusion strip embodiment into the defect shown in FIG. 1.

Turning to FIGS. 1 & 2, depicted is a sternum that has been split into a first sternum section 108 and a second sternum section 109, such as would occur in a sternotomy procedure. The first sternum section 108 includes a void 112 that is present in the cancellous area of the bone. Such a void is a representative example of deficit that would be a criteria to determine a patient in need. An embodiment of a fusion strip 110 is shown that is configured for placement in the void 112. The fusion strip 110 in most instances will lay in the void without the need for any particular securement step. However, in some cases it may be appropriate to hold the fusion strip onto the sternum section such as through the use of a compatable adhesive or through the use of sutures. FIG. 2 shows the fusion strip 110 positioned into the void 112 (hidden). Upon proper placement of the fusion strip 110, the first 108 and second sternum sections are brought together to close upon the fusion strip 110 and secured together through conventional techniques, such as, for example, through the use of a cable, plate, sutures or staples.

In an exemplary embodiment, the fusion strip 110 may be made of demineralized bone matrix processed from a piece of cancellous bone. It should be borne in mind that allogenic sources of tissue are precious and are inherently limited in making certain implant products that have the appropriate osteoconductive and/or osteoinductive features and the appropriate dimensions for a given surgical technique. In the case of allogenic sources of bone, obtaining a continuous piece of cancellous bone from a donor that can produce dimensions suitable for correcting certain defects and or voids at a sternotomy site is not possible. Discussed herein are examples of suitable dimensions of a DBM fusion strip that are achievable from a continuous piece of human cadaveric cancellous bone. In some instances, depending on the size of the defect or void, it is necessary to position more than one fusion strip into the cancellous area of the sternum.

Figure 3:
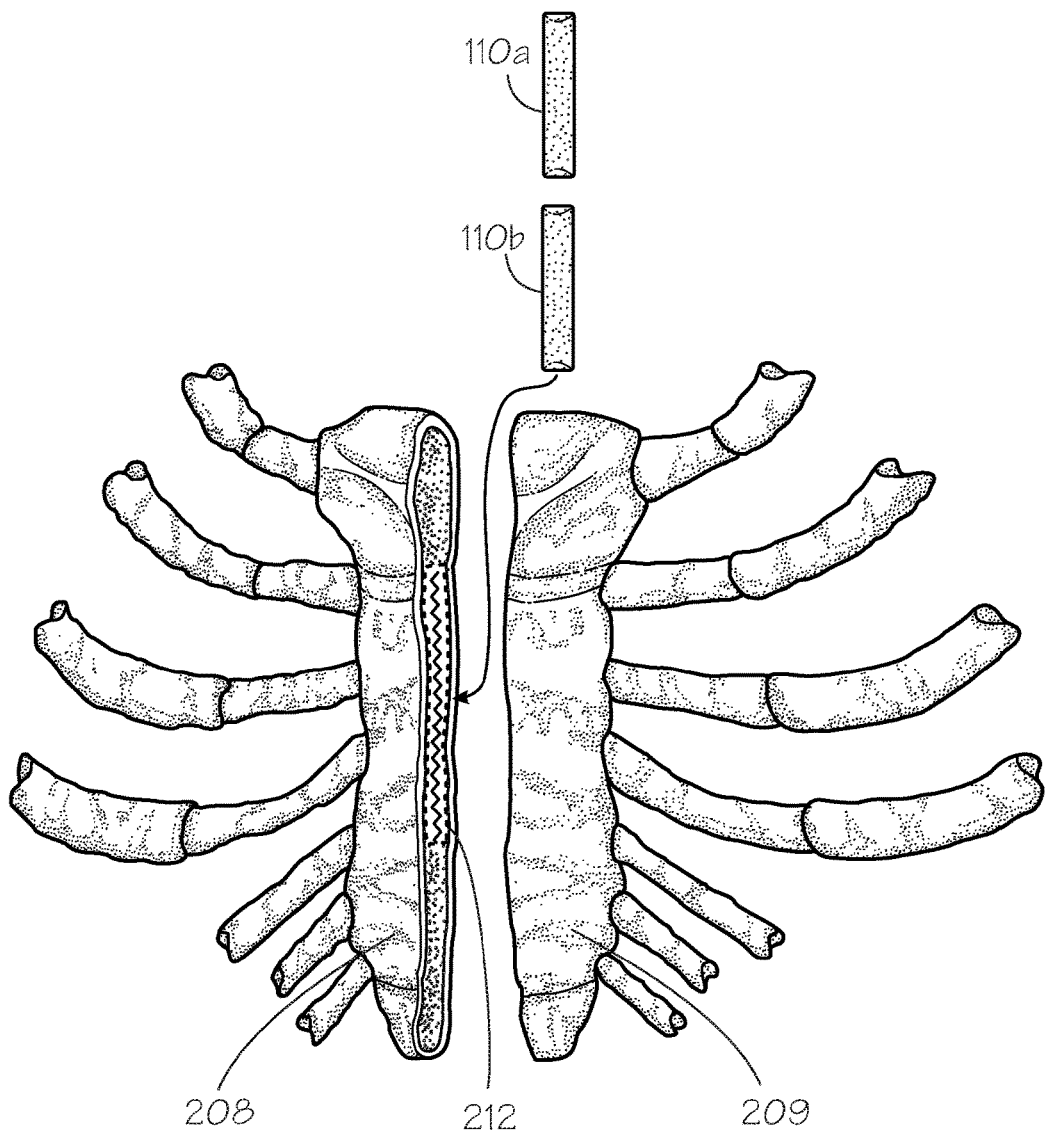
FIG. 3 depicts the use of more than one fusion strip embodiment in a sternotomy procedure in a sternum having a defect.
Figure 4:
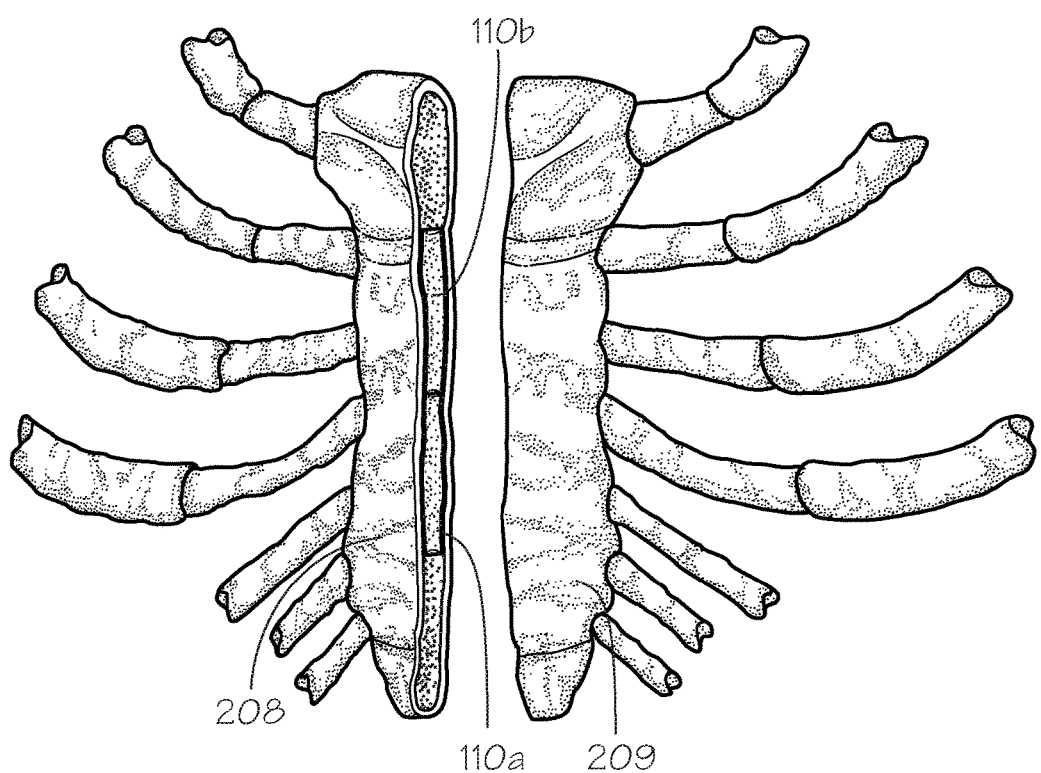
FIG. 4 shows the positioning of two fusion strips into the defect shown in FIG. 3.

FIG. 3 shows an embodiment that includes the implementation of two fusion strips 110a and 110b that are placed adjacent to each other in the sternotomy site between a first sternum section 208 and a second sternum section 209 at a target void 212. FIG. 4 shows the placement of the fusion strips 110a-b at the void 212 (hidden). As discussed above, upon positioning of the fusion strips 110a-b, the first and second sternum sections 208, 209 are closed upon the fusion strips 110a-b and secured together.

Figure 5:
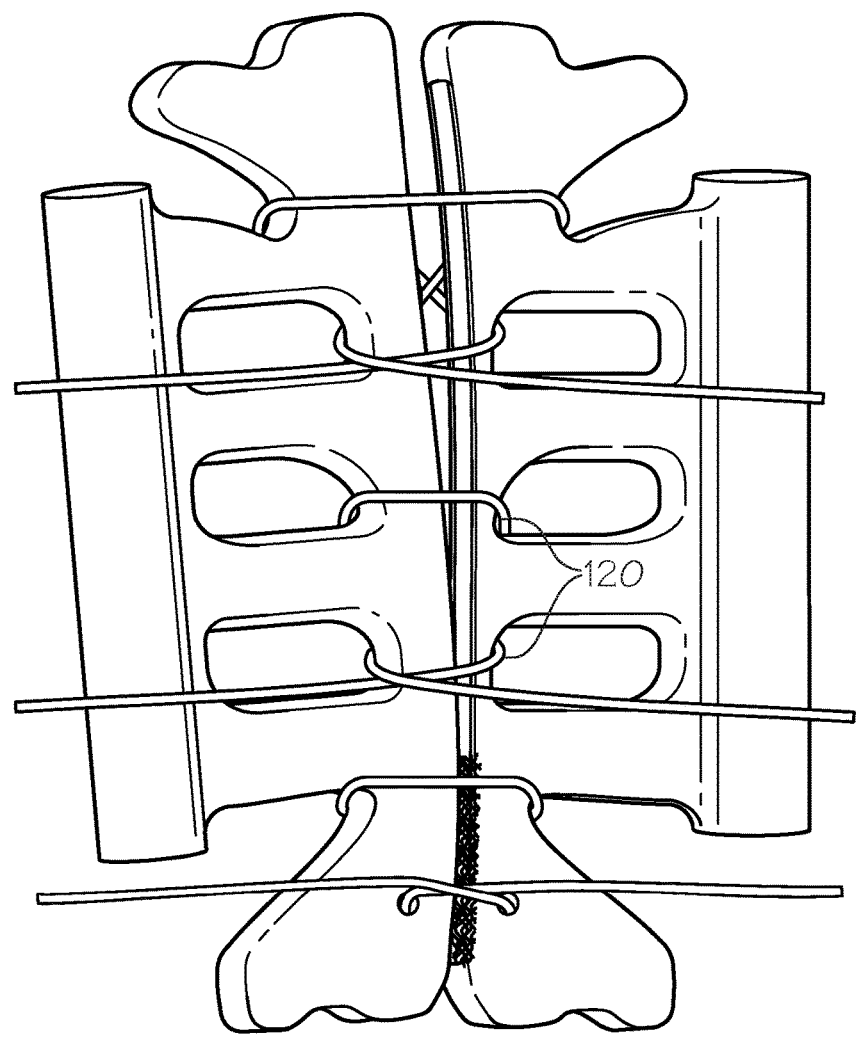
FIG. 5 depicts a placement of a fusion strip into a sternal defect and proximate closure of sternal halves during a sternotomy procedure.
Figure 6:
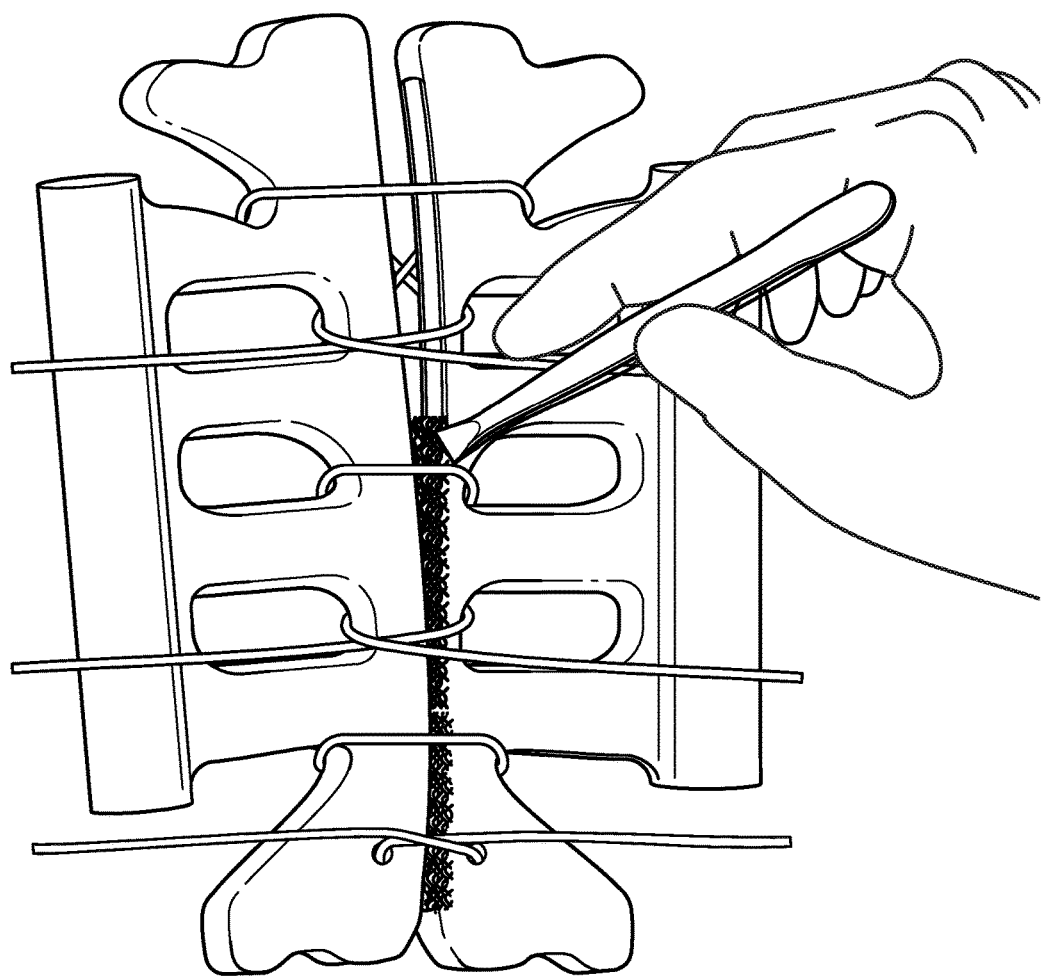
FIG. 6 depicts a sequential placement of a further fusion strip after the stage shown in FIG. 5.

In a specific surgical technique embodiment, a first fusion strip is placed in the void or defect and the proximate region of sternum sections are brought together by the wire to "squeeze" in the fusion strip at that location. Following this tightening, the next fusion strip is placed adjacent to the end of the first fusion strip. Once this next fusion strip is properly placed, the proximate region of the sternum sections are brought together around the next fusion strip portion. It should be noted that at each region of the sternum where a fusion strip is placed, one or more fusion strips could be put in that location. For example, a fusion strip could be put in the void of one sternum half portion and an opposing fusion strip could be put in a void on the opposing sternum half portion across from the other. This depends on the severity of the gaps or voids and the surgeon's discretion. An example of the sequential surgical technique is shown in the photographs of in FIGS. 5 and 6. Also shown in FIGS. 5 and 6 is an example of securement of the first and second sternum sections using a cable 120 technique.

Figure 7:
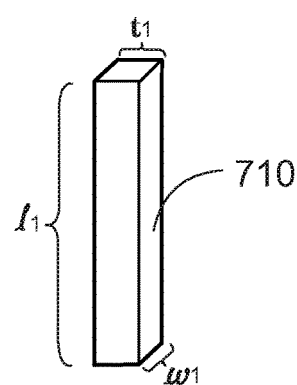
FIG. 7 depicts an example of a fusion strip embodiment in perspective view.
Figure 14A:
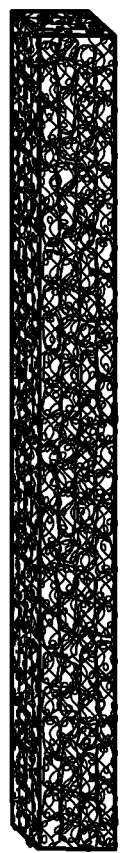
FIG. 14A-B is a photograph of three different fusion strip embodiments made from demineralized cancellous bone.
Figure 14B:
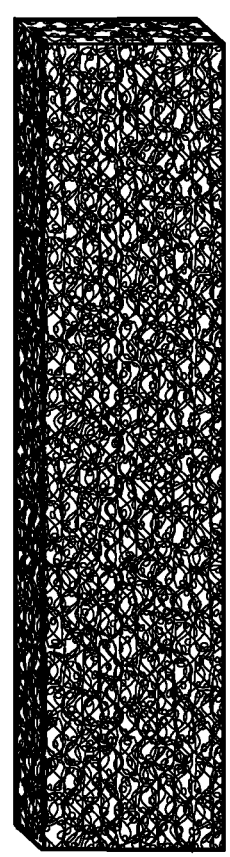

FIG. 14 shows different fusion strip embodiments A and B. These fusion strip embodiments represent demineralized bone matrix (DBM) (cancellous) derived from allograft bone. Typically, the DBM is obtained from processed cancellous bone, as this produces an architecture that is particularly conducive for bone conduction and induction at a sternotomy repair site. As noted above, there is a limit on the dimensions for which allogenic bone can produce. For human cancellous bone, the dimensions that can be produced for a fusion strip embodiment typically fall within the following: 3-20×45-60×3-8 mm (width×length×thickness, represented as $w_1$, $l_1$, and $t_1$, respectively in the fusion strip embodiment 710 shown in FIG. 7) due to anatomical and size limitations. To produce DBM fusion strips from a continuous cancellous bone that have a greater length, these would need to be obtained from xenogenic sources, such as horses or cows that have longer bones. Thus, in another embodiment, the fusion strip used in certain method embodiments is one produced from demineralized cancellous bone obtain from a xenogenic source. The xenogenic based fusion strip may have a dimension of 3-8×65-200×3-8 mm (width×length×thickness).

Figure 8:
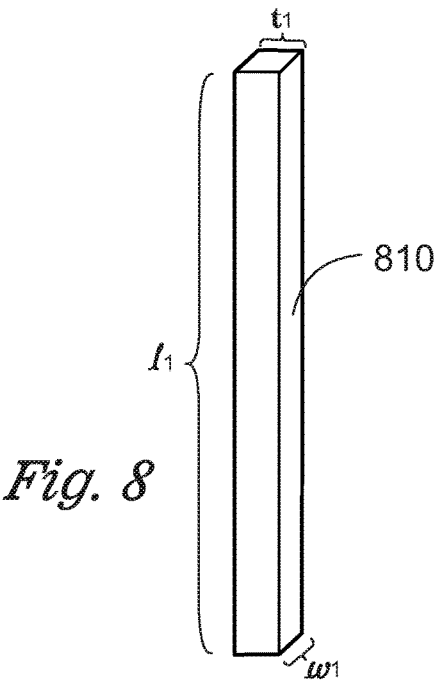
FIG. 8 depicts an example of a fusion strip embodiment in perspective view.

As noted above, certain bone substitute material and/or cortical bone based DBM material may be shaped and formed to possess dimensions that exceed the limits presented by human cancellous bone. FIG. 8 shows an example of a fusion strip 810 that has dimensions exceeding that which is attainable by a continuous piece of human cancellous bone. In this example, $l_1$ is 80-120 mm, $w_1$ is 3-20 mm, and $t_1$ is 3-20 mm. Fusion strip 810 would be particularly useful to repairs defects or voids that extend a great length of the sternum. Fusion strip would typically need to be made from a bone substitute material and/or cortical bone based DBM material.

Figure 9A:
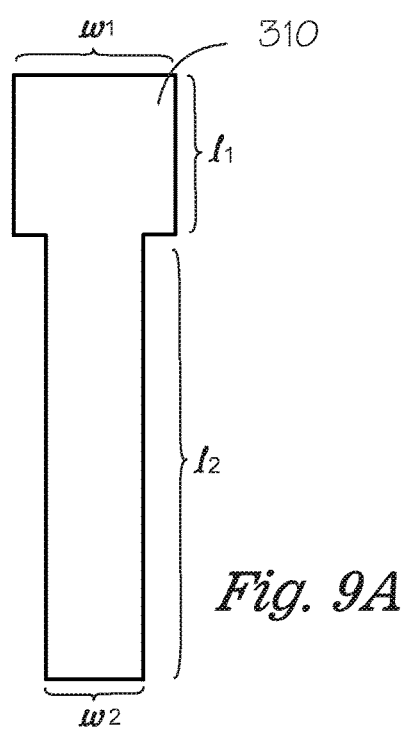
Figure 9B:
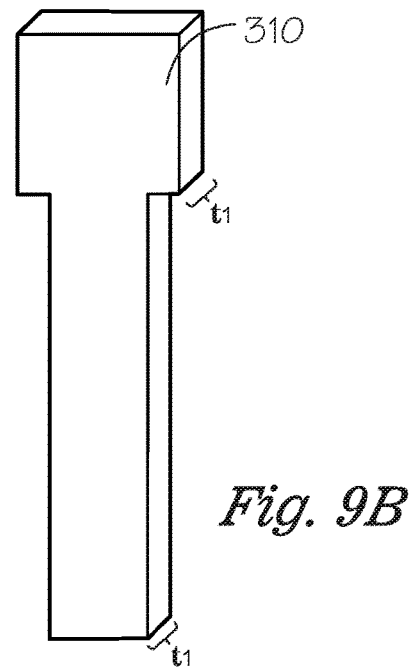

FIG. 9 shows an example of a fusion strip embodiment 310 that has a variable width. FIG. 9a shows a side view of the embodiment 310, where the embodiment 310 has a first width $w_1$ that may be 9-17 mm. In a specific embodiment, $w_1$ is 11-13 mm, or in a more specific embodiment it is approximately 12 mm. The embodiment 310 has a first length $l_1$ that may be 30-100 mm. In a specific embodiment, $l_1$ is 40-60 mm, and in a more specific embodiment it is approximately 50 mm. The embodiment 310 has a second length $l_2$ that may 65 mm-150 mm. In a specific embodiment, $l_2$ is 80-135 mm, and in a more specific embodiment it is approximately 100 mm. The embodiment 310 has a second width $w_2$ that is 3-10 mm. In a specific embodiment, $w_2$ is 4.5-8.5 mm and more specifically is approximately 7 mm. Shown in 9b is a perspective view of the fusion strip embodiment 310. The fusion strip 310 has a first thickness $t_1$ that is 3-10 mm. In a specific embodiment, $t_1$ is 4-8.5 mm and in a more specific embodiment, $t_1$ is approximately 5 mm. In an alternative embodiment, the transition from $w_1$ to $w_2$ along the length of the strip may be a gradual taper as opposed to an orthogonal more abrupt transition.

Figure 15A:
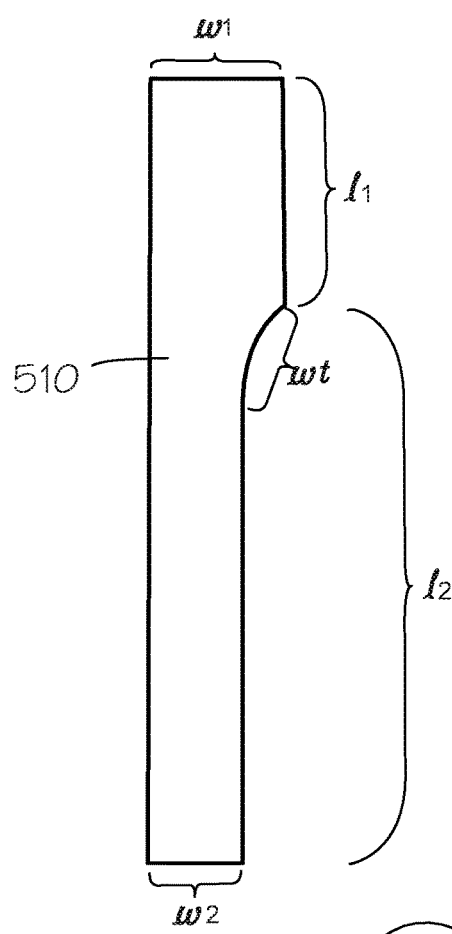
FIG. 15a shows a side view of the width side and FIG. 15b shows the side view of the thickness side.
Figure 15B:
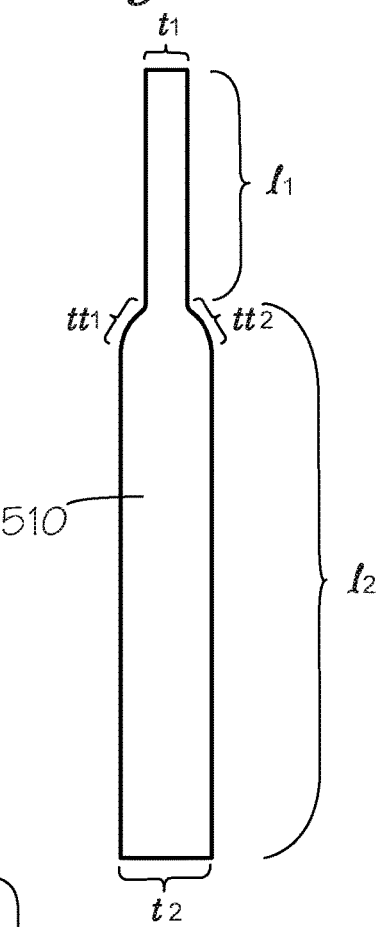

FIG. 15 shows another embodiment 510 that has varied dimensions for both width and thickness dimensions. As shown in FIG. 15a, which is a side view showing the width dimension, the fusion strip 510 includes a first width $w_1$ that may be 9-17 mm. In a more specific embodiment, $w_1$ is approximately 12 mm. The fusion strip 510 includes a second width $w_2$ that may be 3-10 mm. In a specific embodiment, $w_2$ is approximately 7 mm. FIG. 15a also shows that the length $l_1$ of the fusion strip 510 that pertains to $w_1$ may be 30-100 mm. In a specific embodiment, $l_1$ is approximately 50 mm. The length $l_2$ of the fusion strip 510 pertaining to $w_2$ may be 65-150 mm. In a specific embodiment, $l_2$ is approximately 100 mm. As can be seen, the transition wt from the first width $w_1$ to the second width $w_2$ is a gradual taper. It will be understood that the transition wt could be more abrupt such as an orthogonal transition. Shown in FIG. 15b is a different side view of the fusions trip 510 showing the thickness. The fusions trip 510 includes a first thickness $t_1$ that may be 3-10 mm. In a specific embodiment, $t_1$ is 5 mm. The fusion strip 510 includes a second thickness $t_2$ that may be 5-12 mm. In a specific embodiment, t2 is approximately 8. The transition from $t_2$ to $t_1$, $tt_1$ and $tt_2$ is a gradual taper. This could alternatively be a more abrupt transition for $tt_1$ and/or $tt_2$.

Figure 16:
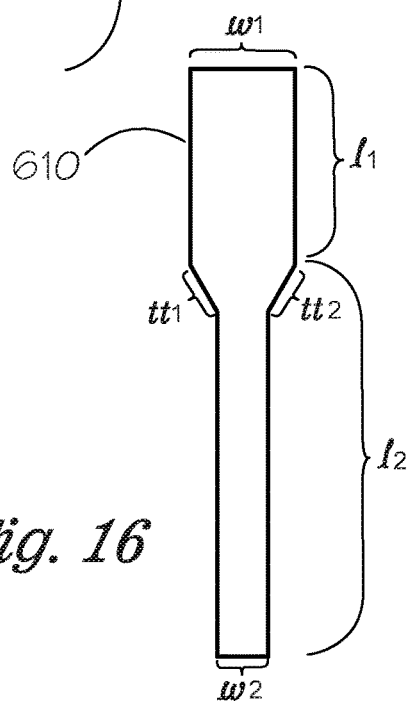
FIG. 16 shows another embodiment of a fusions strip that has varied width and thickness dimensions.

FIG. 16 is a side view showing the width dimension of an alternative embodiment 610 of a fusion strip. The fusion strip 610 includes a $w_1$ and $w_2$ similar to that described for 510 above, with similar dimensions. As shown in FIG. 16, the transition from $w_1$ to $w_2$ is a gradual taper on both sides as noted in $tt_1$ and $tt_2$. The taper occurs proximate to the intersection of $l_1$ and $l_2$. Regarding the thickness dimension of 610, it follows the dimensions that are discussed for 510 in FIG. 15b.

Figure 10:
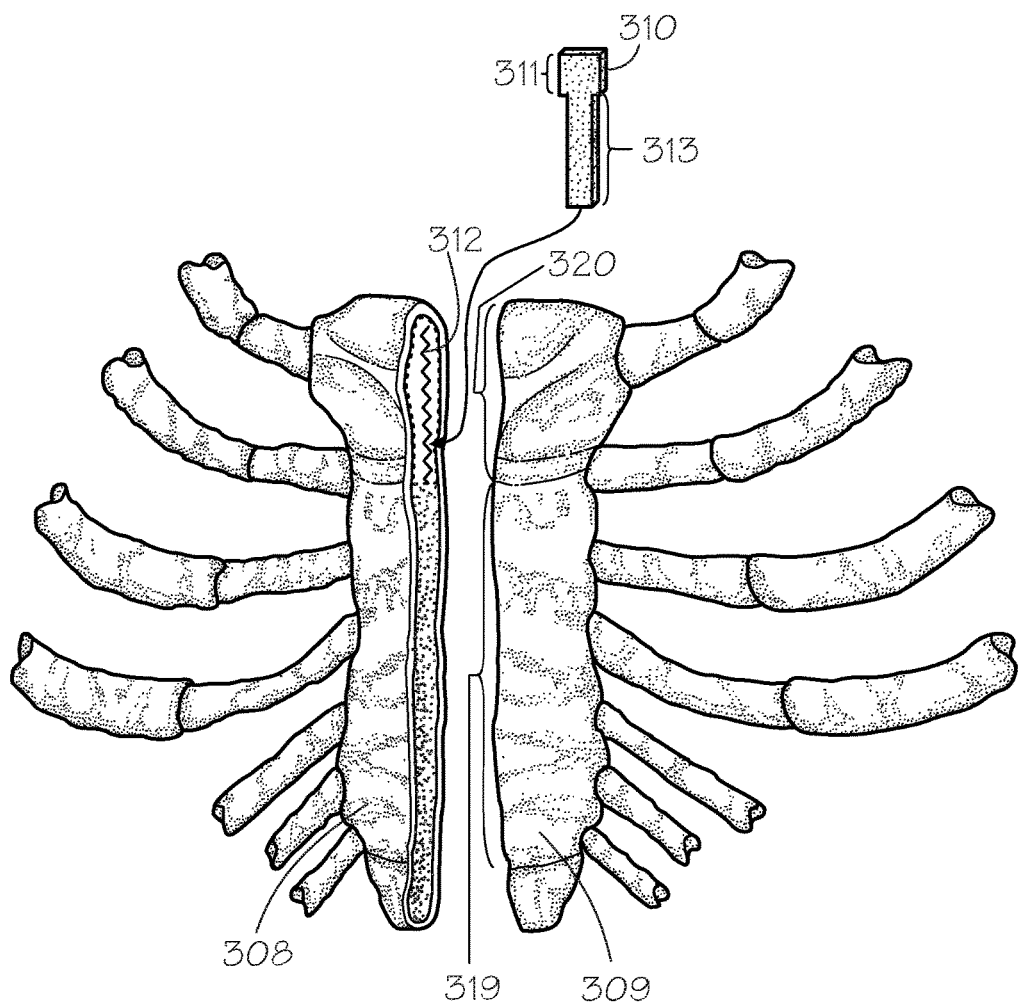
FIG. 10 depicts use of a varied-width fusion strip embodiment in a sternotomy procedure.
Figure 11:
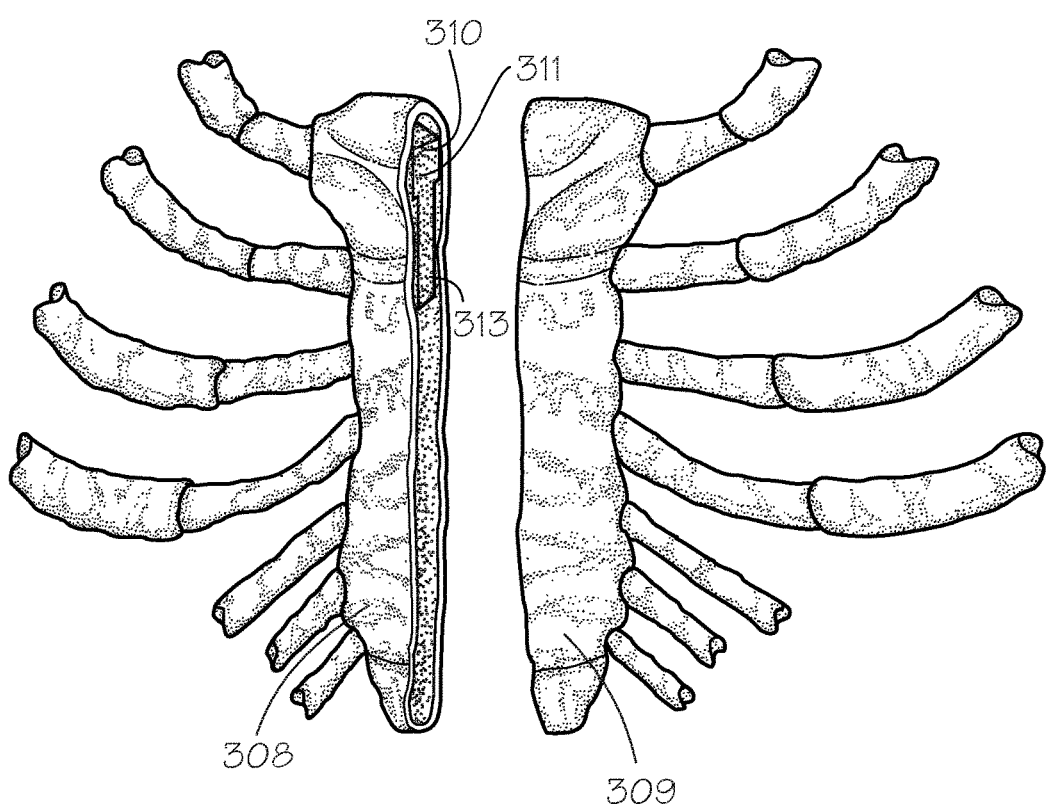
FIG. 11 depicts placement of the varied-width fusion strip embodiment in the defect shown in FIG. 10.

Turning to FIGS. 10 & 11, depicted is a sternum that has been split into a first sternum section 308 and a second sternum section 309. The first sternum section 308 includes a void 312 that is present in the cancellous area of the bone. In this example, the void is present at sternal body 319 as well as the manubrium 320 (which is typically thicker than the sternal body). Such a void is a different representative example of deficit that would be a criteria to determine a patient in need. The fusion strip 310 includes a first section 311 and a section section 313, with the first section 311 being wider. FIG. 11 shows the fusion strip 310 positioned into the void 312 (hidden). The first section 311 sits in the part of the void 312 that is present in the manubrium 320, and the second section sits in the part of the void 312 that is present in the sternal body 319.

Figure 12:
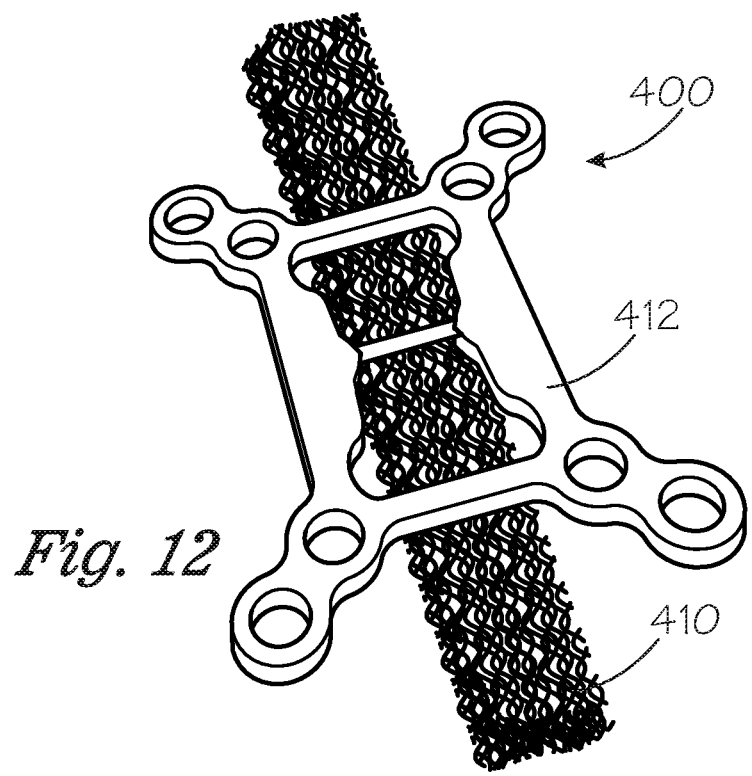
FIG. 12 shows a bottom perspective view of a fusion strip system that includes a fusion strip that is attached to a plate.
Figure 13:
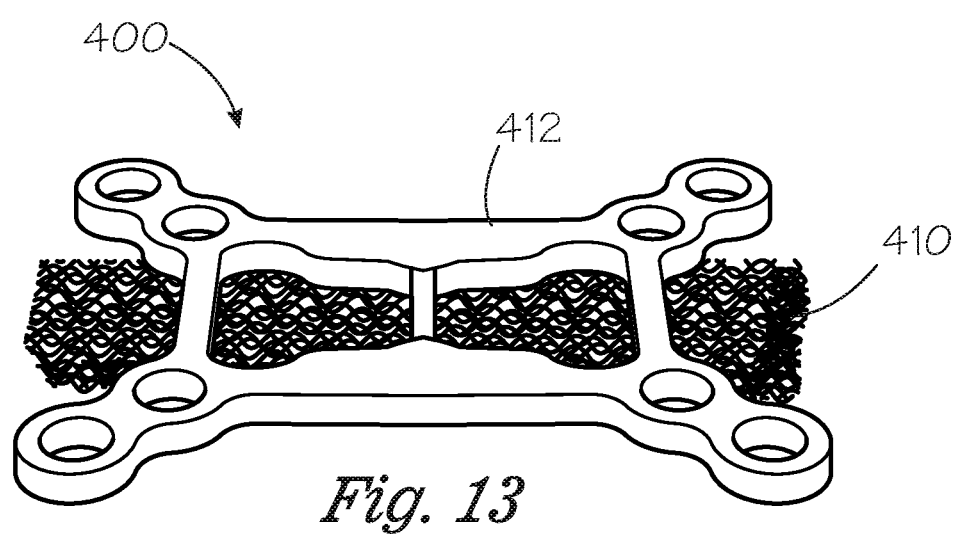
FIG. 13 shows a side perspective view of the embodiment shown in FIG. 12.

FIG. 12 shows a bottom perspective view of a fusion strip system 400. The system 400 includes a fusion strip 410 that is associated with a plate 412. When two sections of a sternum are ready to be closed together, the plate 412 can assist in securing the two sections together while also facilitating repair of a defect or gap in the sternum by provision of the fusion strip 410. FIG. 13 shows a side perspective view of the system 400.

The specific fusion strip embodiments illustrated in the drawings represent cuboidal shapes. However, in light of the teachings herein, those skilled in the art would understand that the fusion strips may take different shapes and forms, including but not limited to, a cylindrical shape, triangular prism shape or be generally cuboidal with rounded edges. For these alternative shapes, the dimensions (width×length× thickness) would generally apply, e.g., width would be the plane that abuts the void or gap in the sternum, length would be the plane that traverses down the sternum, and thickness would be the plane that extends out from gap, void or other defect.

It should be borne in mind that all patents, patent applications, patent publications, technical publications, scientific publications, and other references referenced herein and in the accompanying appendices are hereby incorporated by reference in this application to the extent not inconsistent with the teachings herein.

It is important to an understanding to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While a number of embodiments have been shown and described herein in the present context, such embodiments are provided by way of example only, and not of limitation. Numerous variations, changes and substitutions will occur to those of skilled in the art without materially departing from the invention herein. For example, the present invention need not be limited to best mode disclosed herein, since other applications can equally benefit from the teachings. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

What is claimed is:

1. A method for closing a sternum separated into at least a first sternum section having a first surgical cut site and a second sternum section having a second surgical cut site in a patient, the method comprising:
   i) obtaining a first fusion strip and a second fusion strip, where said first and second fusion strips are comprised of an osteoconductive material and comprise a dimension of 3-12×45-60×3-8 mm (width×length×thickness), wherein the osteoconductive material is comprises of demineralized bone matrix (DBM) comprising cancellous bone such that the DBM retains a natural collagen interconnected porosity architecture of the cancellous bone;
   ii) positioning a first fusion strip into a void or fracture in either said first and second sternum portions at said first and second surgical cut sites, or both;
   iii) positioning a second fusion strip into said void adjacent to an end of said first fusion strip; and
   iv) urging together said first and second sternum portions such that said first and second surgical cut sites are brought together with said first and second fusion strips being in contact with either or both of said first or second surgical cut sites.

2. The method according to claim 1, wherein step i) or step ii), or both, comprise securing said first and/or second fusion strips to one of said first or second sternum portions.

3. The method of claim 2, wherein securing comprises utilizing a suture and/or an adhesive, or mesh.

4. The method of claim 1, further comprising positioning a third fusion strip to said first or second sternum portion, wherein said third fusion strip comprises a dimension of 9-12×45-60×3-8 mm (width×length×thickness).

5. The method of claim 4, wherein said third fusion strip is positioned in a void at the manubrium.

6. The method of claim 4, wherein said third fusion strip comprises a dimension of approximately 10×50×5 mm (width×length×thickness) or approximately 12×50×5 (width×length×thickness).

7. The method of claim 6, wherein said third fusion strip comprises a dimension of 10×50×5 mm or 12×50×5 mm.

8. The method of claim 1, wherein at least one of said first fusion strip or second fusion strip is comprised of DBM.

9. The method of claim 8, wherein said DBM is demineralized cancellous bone.

10. The method of claim 1, wherein said first and/or second fusions strips comprise a dimension of is approximately 5×50×5 mm or approximately 7×50×5 mm.

11. The method of claim 10, wherein said first and/or second fusions strips comprise a dimension of 5×50×5 mm or 7×50×5 mm.

12. The method of claim 1, wherein at least one of said first and second fusion strips comprise bone morphogenetic protein.

13. A method for closing a sternum separated into at least a first sternum section having a first surgical cut site and a second sternum section having a second surgical cut site in a patient in need thereof, wherein the sternum comprises a fracture or void, the method comprising:

i) positioning at least one fusion strip into the void or fracture in either said first and second sternum portions at said first and second surgical cut sites, or both, wherein the at least one fusion strip is comprised of an osteoconductive material and comprise a dimension of 3-8×45-60×3-8 mm (width×length×thickness) or 3-8×65-200×3-8 mm (width×length×thickness), wherein the osteoconductive material is comprises of demineralized bone matrix (DBM) comprising cancellous bone such that the DBM retains a natural collagen interconnected porosity architecture of the cancellous bone; and ii) urging together said first and second sternum portions such that said first and second surgical cut sites are brought together with said at least one fusion strip being in contact with either or both of said first or second surgical cut sites.

14. The method of claim 13, wherein said at least one fusion strip is associated with a plate, wherein the plate assists in securing together the first and second sternum sections with the at least one fusion strip sandwiched between the first and second surgical cut sites.

* * * * *